United States Patent
Kim et al.

(10) Patent No.: US 12,408,604 B2
(45) Date of Patent: Sep. 9, 2025

(54) METHOD FOR PRODUCING AVENANTHRAMIDE-RICH OATS USING ACTIVE ELICITORS

(71) Applicant: KOREA RESEARCH INSTITUTE OF BIOSCIENCE AND BIOTECHNOLOGY, Daejeon (KR)

(72) Inventors: Cha Young Kim, Daejeon (KR); Yu Jeong Jeong, Daejeon (KR); Jae Cheol Jeong, Daejeon (KR); Soyoung Kim, Daejeon (KR); Tae Hee Kim, Daejeon (KR); Sung Chul Park, Daejeon (KR); Jiyoung Lee, Daejeon (KR); Suk Weon Kim, Daejeon (KR); Suhyun Park, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 17/995,648

(22) PCT Filed: Apr. 7, 2021

(86) PCT No.: PCT/KR2021/004318
§ 371 (c)(1),
(2) Date: Oct. 6, 2022

(87) PCT Pub. No.: WO2021/206436
PCT Pub. Date: Oct. 14, 2021

(65) Prior Publication Data
US 2023/0172131 A1 Jun. 8, 2023

(30) Foreign Application Priority Data

Apr. 7, 2020 (KR) .................. 10-2020-0042387

(51) Int. Cl.
*A01H 1/06* (2006.01)
*A01H 6/46* (2018.01)

(52) U.S. Cl.
CPC .................. *A01H 1/06* (2013.01); *A01H 6/46* (2018.05)

(58) Field of Classification Search
None
See application file for complete search history.

(56) References Cited

FOREIGN PATENT DOCUMENTS

| KR | 1020110131316 A | 12/2011 | | |
|---|---|---|---|---|
| KR | 1020150047790 A | 5/2015 | | |
| KR | 1020180044048 A | 5/2018 | | |
| KR | 1020190104817 A | * | 9/2019 | ............. A23L 33/10 |

OTHER PUBLICATIONS

Soriano et al, Inducible Flavone in Oats (*Avena sativa*) Is a Novel Defense Against Plant-Parasitic Nematodes 2004, Phytopathology 94: 1207-1214. (Year: 2004).*
Ogura et al, Induction of Hydroxycinnamic Acid Amides and Tryptophan by Jasmonic Acid, Abscisic Acid and Osmotic Stress in Barley Leaves 2001, Z. Naturforsch C. J. Biosci. 56: 193-202 (Year: 2001).*
Muroi et al, Accumulation of hydroxycinnamic acid amides induced by pathogen infection and identification of agmatine coumaroyltransferase in *Arabidopsis thaliana* 2009, Planta 230: 517-527 (Year: 2009).*
Liu et al, The Role of Hydroxycinnamic Acid Amide Pathway in Plant Immunity 2022 Frontiers in Plant Science 13:922119, pp. 1-11. (Year: 2022).*
Kim et al, 2021, International Journal of Molecular Sciences 22:4779 (Year: 2021).*
Oregon State University, 2024, Germination and Seedling Emergence, forages.oregonstate.edu/regrowth/how-does-grass-grow/developmental-phases/vegetative-phase/germination-and-seedling (Year: 2024).*
Baenas et al, 2014, Molecules 10: 13541-13563 (Year: 2014).*
Li et al, 2019, Metabolites 163: 1-12 (Year: 2019).*
Yang et al, 2018, Plant Cell Physiology 59(11): 2381-2393 (Year: 2018).*
International Search Report for International Application No. PCT/KR2021/004318 dated Aug. 13, 2021, 8 pages including English Translation.
Ogura et al., "Induction of Hydroxycinnamic Acid Amides and Tryptophan by Jasmonic Acid, Abscisic Acid .and Osmotic Stress in Barley Leaves," Z. Naturforsch C. J. Biosci., 2001, vol. 56c, pp. 193-202.

* cited by examiner

Primary Examiner — Brent T Page
Assistant Examiner — Aleksandar Radosavljevic
(74) Attorney, Agent, or Firm — MH2 Technology Law Group, LLP (57) ABSTRACT

The present invention relates to a method for producing oats having high-content avenanthramides using elicitors.

11 Claims, 4 Drawing Sheets
Specification includes a Sequence Listing.

FIG. 7

METHOD FOR PRODUCING AVENANTHRAMIDE-RICH OATS USING ACTIVE ELICITORS

CROSS-REFERENCE TO RELATED APPLICATIONS

This application is a U.S. National Stage application of PCT/KR2021/004318 filed 7 Apr. 2021, which claims priority to Korean Patent Application No. 10-2020-0042387 filed 7 Apr. 2020, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 6 Oct. 2022, is named 0363_0021_PCT_US_SL.txt and is 3 Kilobytes in size.

TECHNICAL FIELD

The present invention relates to a method for producing oats having high-content avenanthramides using elicitors.

BACKGROUND ART

Compared to other grains, oats are rich in proteins and lipids and contain a large amount of unsaturated fatty acids. In addition, the oats are rich in essential amino acids such as lysine, vitamin B group, vitamin E, and minerals, and contain a large amount of beta-glucan, a dietary fiber, and thus the oats are recognized as a crop with very high sitologic value. In this regard, a variety of oats have been developed in Korea, and research to increase the extraction efficiency of active ingredients contained in oats is also continuing.

Various types of active ingredients exist in oats, and avenanthramides, a specific antioxidant ingredient of oats, are known to be effective in inflammatory diseases (Sur, Runa et al. (2008) Avenanthramides, polyphenols from oats, exhibit anti-inflammatory and anti-itch activity. Archives of dermatological research. 300. 569-74.). In addition, the avenanthramides are known as powerful antioxidants and have been reported to be effective in regulating blood pressure. In addition, it has been known that the avenanthramides may exhibit effects on skin irritation suppression and anti-arteriosclerosis, and the like, and recently, it has been found that the avenanthramides may be used in the treatment of hearing loss, neurodegenerative diseases, and the like. As such, studies on the use of avenanthramides have been actively conducted, and the avenanthramides are spotlighted as useful ingredients that can be used in the treatment of various diseases. Accordingly, the demand for a method capable of increasing the production of avenanthramides is increasing.

SUMMARY OF INVENTION

Technical Problem

The present inventors confirmed that the content of avenanthramides in oats may be significantly increased when any one or more elicitors of methyl jasmonate and abscisic acid were treated, and then completed the present invention.

Solution to Problem

An object of the present invention is to provide a method for producing oats having high-content avenanthramides, including treating any one or more elicitors of methyl jasmonate and abscisic acid; and a method of enhancing the expression of avenanthramide biosynthetic genes in oats.

Another object of the present invention is to provide a method for increasing the production of avenanthramides including any one or more elicitors of methyl jasmonate and abscisic acid; and a composition for enhancing the expression of avenanthramide biosynthetic genes.

Advantageous Effects of Invention

By using the production method of the present invention, it is possible to significantly increase the content of avenanthramides, which are useful ingredients of oats, and furthermore, it is possible to usefully used in the preparation of pharmaceuticals, health functional foods, and the like containing the avenanthramides.

BRIEF DESCRIPTION OF DRAWINGS

FIG. 2 illustrates a result of treating distilled water (DW), ethanol (EtOH), methyl viologen (MV), methyl jasmonate (MJ), abscisic acid (ABA), salicylic acid (SA), ethephon (ET), and chitosan (CHI) in the order of a horizontal axis.

DESCRIPTION OF EMBODIMENTS

Specifically, this will be described as follows. Meanwhile, each description and embodiment disclosed in the present invention can also be applied to each of other descriptions and embodiments. That is, all combinations of various components disclosed in the present invention belong to the scope of the present invention. In addition, the specific description described below may not limit the scope of the present invention.

Further, those skilled in the art may recognize or determine a plurality of equivalents to specific embodiments of the present invention described in the present invention by using only a general experiment. In addition, such equivalents are intended to be included in the present invention.

An aspect of the present invention provides a method for producing oats having high-content avenanthramides including treating oats with any one or more elicitors of methyl jasmonate and abscisic acid.

As used herein, the term "avenanthramide" is an alkaloid-based compound known to be mainly produced in oats. The avenanthramide may be any one or more selected form the group consisting of avenanthramide A, avenanthramide B, avenanthramide C, avenanthramide O and avenanthramide P. Specifically, the avenanthramide may mean one or more ingredients selected from the group consisting of avenanthramide A, avenanthramide B, and avenanthramide C, but is not limited thereto.

The avenanthramide may also be referred to as anthranilic acid amide and may be represented by the following Chemical Formula 1:

[Chemical Formula 1]

In Chemical Formula 1, a compound, in which n=1, R1 is H, R2 is OH, R3 is H, R4 is OH, and R5 is H, may be referred to as "avenanthramide A", a compound, in which n=1, R1 is H, R2 is OH, R3 is OCH3, R4 is OH, and R5 is H, may be referred to as "avenanthramide B", and a compound, in which n=1, R1 is H, R2 is OH, R3 is OH, R4 is OH, and R5 is H, may be referred to as "avenanthramide C".

In addition, it has been known that the avenanthramides may exhibit effects on anti-inflammatory, antioxidant, itch suppression, skin irritation suppression, anti-arteriosclerosis, and the like, and recently, it has been found that the avenanthramides may be used in the treatment of hearing loss, neurodegenerative diseases, and the like. Therefore, the method for producing oats having high-content avenanthramides of the present invention may be usefully used in preparing, developing, and researching therapeutic agents for the diseases.

As used herein, the term "elicitor" generally refers to a substance having an activating action of a biological defense mechanism. For the purpose of the present invention, the elicitors may increase the content of avenanthramides in oats, and may include methyl jasmonate and/or apsis acid.

Specifically, the elicitors may be any one or more of methyl jasmonate and abscisic acid.

The term "methyl jasmonate" as used herein is also abbreviated as MeJA and may also be referred to as "MJ" in the present invention. The methyl jasmonate is a type of volatile organic compound and is known to be synthesized by a defense system in some plants. The methyl jasmonate may have a structure of the following Chemical Formula 2:

[Chemical Formula 2]

As used herein, the term "abscisic acid" is a kind of plant hormone also abbreviated as ABA, and is known to be produced when plants respond to environmental stress. The abscisic acid may have a structure of the following Chemical Formula 3:

[Chemical Formula 3]

The methyl jasmonate and the abscisic acid have various roles in the plants, and are known that effects thereof vary depending on a type of plant.

Figure 2:
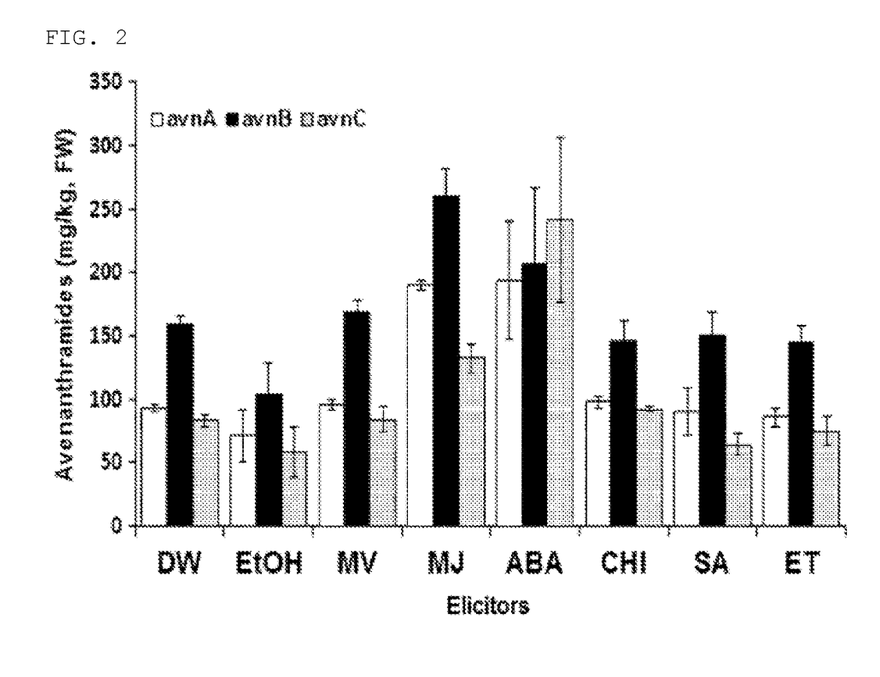
FIG. 2 illustrates a comparison of the synthesis amounts of avenanthramides A, B, and C through the treatment with elicitors in oats.
Figure 6:
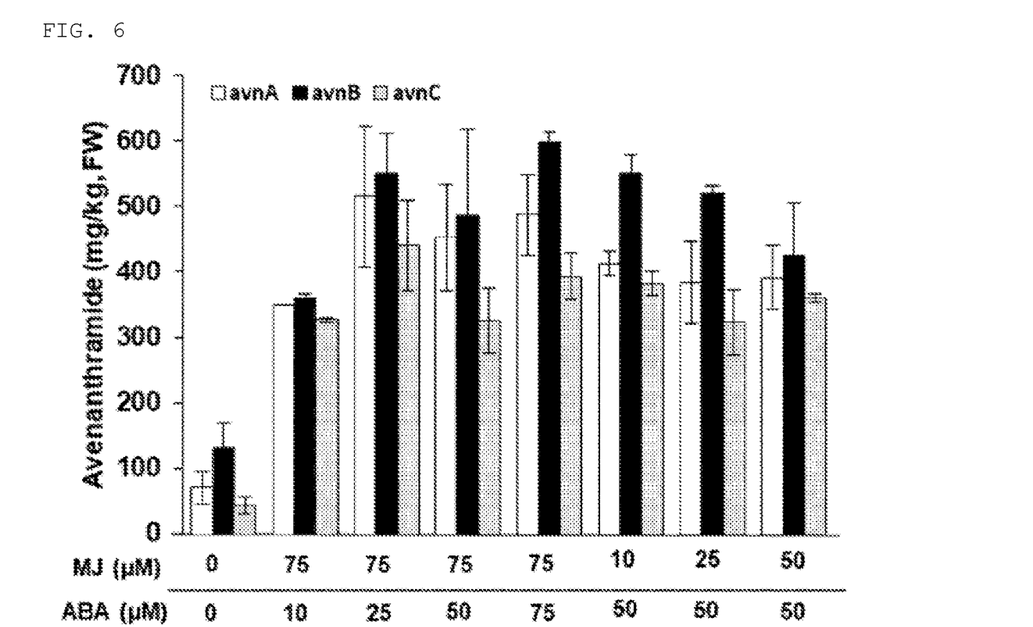
FIG. 6 illustrates a result of confirming the production of avenanthramides by HPLC analysis by treating two types of elicitors MJ and ABA together.
Figure 7:
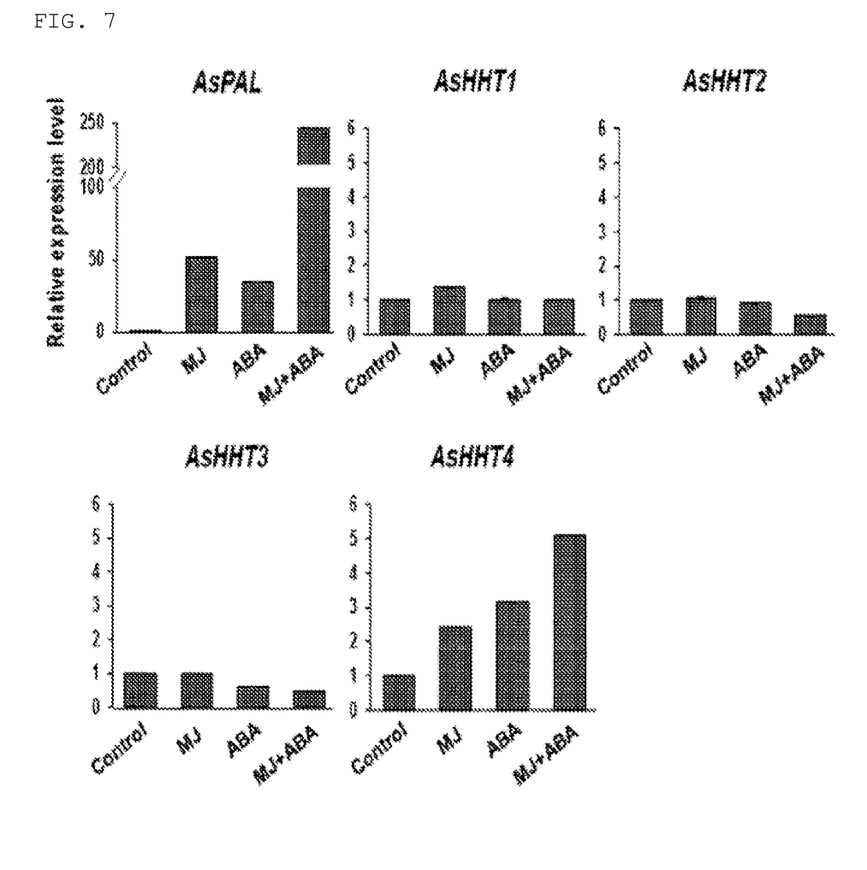
FIG. 7 illustrates a result of analyzing the transcriptional expression of avenanthramide biosynthetic genes PAL and HHT when treating two elicitors MJ and ABA together.

In an embodiment of the present invention, as a result of confirming the content of avenanthramides by treating oats with various types of elicitors, it was confirmed that the content of avenanthramides in oats increased most when treated with methyl jasmonate or abscisic acid (FIG. 2). In addition, it was confirmed that the content of avenanthramides in oats may greatly increase when treated with both methyl jasmonate and abscisic acid (FIG. 6).

The methyl jasmonate and/or abscisic acid may be treated at an appropriate concentration within the range having the effect of increasing the content of avenanthramides in oats.

In an embodiment, the method for producing oats having high-content avenanthramides of the present invention may include treating the methyl jasmonate at a concentration of 5 uM to 200 uM. Specifically, the methyl jasmonate may be treated at a concentration of 10 uM to 100 µM, 20 uM to 100 µM, 25 uM to 100 uM, or 50 uM to 100 uM, but is not limited thereto.

In an embodiment, the method for producing oats having high-content avenanthramides of the present invention may include treating the abscisic acid at a concentration of 5 uM to 400 uM. Specifically, the abscisic acid may be treated at a concentration of 10 uM to 300 uM, but is not limited thereto.

In an embodiment, the method for producing oats having high-content avenanthramides of the present invention may include treating both the methyl jasmonate and the abscisic acid. In this case, the methyl jasmonate and the abscisic acid may be treated in an appropriate ratio within the range of increasing the content of avenanthramides. For example, the methyl jasmonate and the abscisic acid may be treated in a concentration ratio (molar ratio) of 20 to 1:1, and for example, the methyl jasmonate to the abscisic acid may be treated in a concentration ratio of 4 to 1:1, but is not limited thereto.

In the method for producing oats having high-content avenanthramides of the present invention, the oats may be germinated oats, but is not limited thereto. The germination is a phenomenon in which seeds, spores, pollen, and sprouts growing on branches or roots of plants start to develop or grow.

The method for producing oats having high-content avenanthramides of the present invention may be treating the elicitors for 12 to 144 hours after inducing the germination of oats. Specifically, the elicitors may be treated for 24 hours to 120 hours, but is not limited thereto.

In the method for producing oats having high-content avenanthramides of the present invention, the treating the oats with the elicitors may include culturing oats in the presence of elicitors. For example, the oats may be cultured in the presence of elicitors by spraying the elicitors themselves or a solution containing the elicitors in oat seeds or germinated oats, or by treating the elicitors in the culture solution. The "culturing" may be used interchangeably with "cultivating".

In the method for producing oats having high-content avenanthramides of the present invention, the "oats having high-content avenanthramides" mean oats containing avenanthramides with a high content. This may mean that the content of avenanthramides is higher than that of oats not treated with elicitors. For example, this may mean that the content of avenanthramides is increased compared to oats not treated with methyl jasmonate and/or abscisic acid, but is not limited thereto.

Another aspect of the present invention provides a method for producing an oat extract having high-content avenanthramides including culturing oats by treating any one or more elicitors of methyl jasmonate and abscisic acid; and obtaining an extract or fraction of the oats.

The extract includes the extract itself and all formulated extracts formable using the extract, such as an extract obtained by extracting oats, a dilute or concentrate of the extract, a dried product obtained by drying the extract, a modified or purified product of the extract, or a mixture thereof.

The extraction method of the extract is not particularly limited, and may be extracted according to a method commonly used in the art. Non-limiting examples of the extraction method may include a hydrothermal extraction method, an ultrasonic extraction method, a filtration method, a reflux extraction method, and the like, and these methods may be performed alone or in combination with two or more methods. The type of an extraction solvent is not particularly limited, and any solvent known in the art may be used.

The fraction refers to a result obtained by performing fraction to separate a specific ingredient or a specific ingredient group from a mixture including various ingredients. The fraction method for obtaining the fraction of the present invention may be performed according to a method commonly used in the art, and examples of the fraction method include a method for obtaining a fraction from the extract by treating the extract of the present invention with a predetermined solvent, a method for immersing and recovering polysaccharides for the extract using a cold soaking method and a centrifugation method, and the like, but are not limited thereto.

Another aspect of the present invention provides a method for producing avenanthramides including culturing oats by treating any one or more elicitors of methyl jasmonate and abscisic acid; obtaining an extract or fraction of the oats; and obtaining avenanthramides from the extract or fraction.

The obtaining of the avenanthramides from the extract or fraction may include isolating and/or purifying the avenanthramides from the extract or fraction. For the separation and/or purification, methods commonly used in the art of the present invention may be used, and as non-limiting examples, methods such as chromatography may be used. The purification may also be performed by only one method, or also by two or more methods together.

Another aspect of the present invention provides a method for increasing the expression of avenanthramide biosynthetic genes in oats including culturing oats by treating any one or more elicitors of methyl jasmonate and abscisic acid.

The "avenanthramide biosynthesis gene" refers to a gene encoding an enzyme involved in avenanthramide biosynthesis. Specifically, the avenanthramide biosynthesis gene may be a gene encoding an enzyme for synthesizing avenanthramides from a precursor, and examples of the enzyme include hydroxycinnamoyl-CoA: hydroxyanthranilate N-hydroxycinnamoyl transferase (HHT), 4-coumarate:coenzyme A ligase (4CL), caffeoyl-CoA O-methyltransferase (CCoAOMT), phenylalanine ammonia lyase (PAL), and the like. However, the present invention is not limited thereto.

In an embodiment of the invention, it was confirmed that when the methyl jasmonate and/or abscisic acid was treated, the expression levels of a PAL gene encoding PAL and a HHT4 gene encoding HHT were increased, and it was confirmed that the expression of avenanthramides biosynthesis genes in oats was increased when the oats were cultured by treating the elicitors of the present invention.

Another aspect of the present invention provides a composition for increasing the production of avenanthramides including any one or more elicitors of methyl jasmonate and abscisic acid.

As described above, since any one or more elicitors of methyl jasmonate and abscisic acid increase the content of avenanthramides in the oats, the composition including the elicitors may be used as a composition for increasing the production of avenanthramides.

Another aspect of the present invention provides a composition for enhancing the expression of avenanthramide biosynthetic genes including any one or more elicitors of methyl jasmonate and abscisic acid.

As described above, since any one or more elicitors of methyl jasmonate and abscisic acid increase the expression of avenanthramide biosynthetic genes in the oats, the composition including the elicitors may be used as a composition for enhancing the expression of avenanthramide biosynthetic genes.

Another aspect of the present invention provides a use of a composition including any one or more elicitors of methyl jasmonate and abscisic acid for increasing the production of avenanthramides.

Another aspect of the present invention provides a use of a composition including any one or more elicitors of methyl jasmonate and abscisic acid for producing oats having high-content avenanthramides.

The elicitors, the avenanthramides, and the production of the oats having high-content avenanthramides are the same as described above.

[Embodiments]

Hereinafter, the present invention will be described in more detail with reference to Examples and Experimental Examples. However, these Examples and Experimental Examples are only illustrative the present invention, and the scope of the present invention is not limited to these Examples and Experimental Examples.

EXAMPLES

Example 1: In Vitro Culture Conditions of Oats, Extraction of Avenanthramides, and HPLC Analysis Method In an embodiment of the present invention, a domestic cultivated breed, Choyang oats, was used. The Choyang oat seeds were immersed for 12 hours, and then sterilized at 50° C. for 10 minutes and used. Two sheets of sterile filter paper were laid on a plant culture dish, poured with 7 ml of water, and then the sterilized Choyang oat seeds were placed and cold-treated at 4° C. for two days. The Choyang oat seeds were cultured under culture conditions of 25° C. and a photoperiod of 16L:8D.

Analysis of avenanthramides of germinated oats recovered in Example of the present invention was performed as follows. First, the obtained germinated oats were powdered using liquid nitrogen. 0.1 g of the oat powder was extracted with 1 ml of 80% methanol, and then sonicated at 50° C. for 20 minutes, extracted, and then centrifuged to obtain an oat extract from an upper layer. The extracted filtrate was dried by injecting air, and the dried product was dissolved in 200 μl of 80% methanol, and filtered using 0.2 μm PTFE (hydrophilic, ADVANTEC, Japan), and the sample was used for high-performance liquid chromatography (HPLC) analysis. A pump system used 4 solvent pumps (quaternary pumps), and a column used ZORBAX SB-18 (5 mm, 4.6×150 mm) from Agilent, and a mobile phase was analyzed by using gradient elution using water (A, 5% acetonitrile, 0.1% formic acid) and acetonitrile. (B, 0.1% formic acid).

Example 2: Analysis of Production of Avenanthramides by Period During Germination Process of Oats In order to confirm a change in production of avenanthramides during the germination process of oats, germination was induced under the culture conditions of Example 1, and the production of avenanthramides by germination period of oats was analyzed at intervals of 24 hours.

After the cold treatment, the extraction was performed after harvesting from 0 hour, which is the start of the culture, for 5 days at intervals of 24 hours. For the extraction of avenanthramides, the harvested oats were pulverized using liquid nitrogen, and 0.1 g of the pulverized sample was added with 1 ml of 80% methanol, extracted by ultrasonication at 50° C. for 20 minutes, and used.

Figure 1:
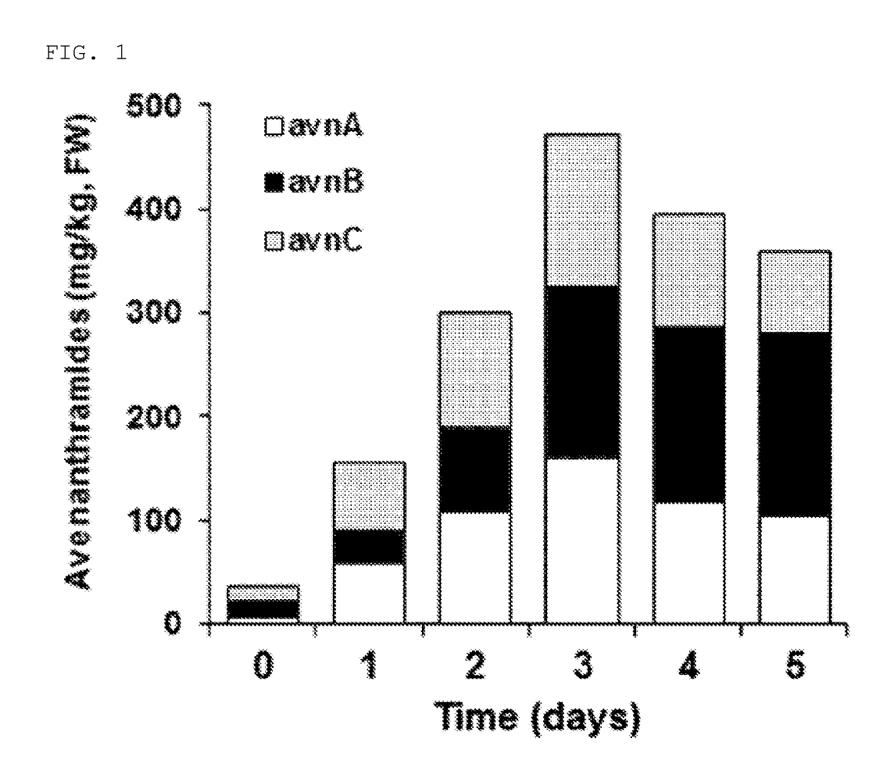
FIG. 1 illustrates a result of confirming the content of avenanthramides in a process of growing oats through in vitro culture.

As a result, it was confirmed that the production of avenanthramides increased from day 1 after germination to day 3 after germination, and at most 470 mg/kg of avenanthramides were produced on the day 3 after germination (FIG. 1).

Example 3: Comparison of Production of Avenanthramides in Oats when Treated with Various Elicitors Experiments were conducted to discover elicitors capable of most increasing the production of avenanthramides.

Based on the results confirmed in Example 1, elicitors were treated on day 2 after germination induction in which the accumulation of avenanthramides was stably increased.

After treatment with the elicitors for 3 days, the avenanthramides were harvested and HPLC was performed. The elicitors used at this time were methyl jasmonate (MJ), abscisic acid (ABA), salicylic acid (SA), ethephon (ET), methyl viologen (MV), and chitosan (CHI). DW was used as a solvent for MV, CHI, and SA, and EtOH was used as a solvent for ET, MJ, and ABA. A case of treating only DW and EtOH (0.1%), which are solvents of each elicitor, was set as a control. The experimental results were shown in Table 1 and FIG. 2 below.

TABLE 1

|  | mg/kg, FW | | | | Compared to control |
| --- | --- | --- | --- | --- | --- |
|  | avnA | avnB | avnC | total |  |
| DW (Control) | 93.27 | 159.61 | 83.08 | 335.96 |  |
| MV | 95.37 | 169.01 | 84.14 | 348.52 | 3.74% |
| CHI | 97.87 | 145.67 | 92.11 | 335.65 | −0.09% |
| SA | 90.53 | 149.58 | 64.34 | 304.45 | −9.38% |
| EtOH (Control) | 71.07 | 103.2 | 58.3 | 232.57 |  |
| ET | 86 | 145.36 | 74.96 | 306.32 | 31.71% |
| MJ | 190.07 | 260.43 | 132.39 | 582.89 | 150.63% |
| ABA | 193.78 | 207.37 | 241.72 | 642.87 | 176.42% |

As a result, it was confirmed that when treated with some elicitors such as CHI and SA, the effect was slightly decreased compared to a control group DW, whereas the production of avenanthramides was significantly increased compared to a control group EtOH when MJ and ABA were treated (FIG. 2). In addition, it was confirmed that the production of avenanthramide C was specifically increased the most when ABA was treated.

Example 4: Analysis of Expression of Avenanthramide Biosynthesis Genes in Oats when Treated with Various Elicitors It was confirmed how the expression of avenanthramides biosynthesis genes in oats was changed by the various elicitors treated in Example 3.

Specifically, total RNA was isolated from the recovered oats, and cDNA was synthesized from the isolated total RNA using a First-Strand CDNA Synthesis Kit (Fermantas, Canada). By using the synthesized cDNA, qRT-PCR was performed on avenanthramide biosynthesis-related genes.

For the qRT-PCR amplification, a Quick Guide from BIOFACT was used, and a process of initial denaturation at 95° C. for 15 minutes and denaturation at 95° C. for 20 seconds, binding and elongation at 60 seconds for 40 seconds was repeated 40 times, and melting curve analysis was performed at 65° C. to 95° C. by 1° C. for 0.5 second.

Primers for avenanthramides biosynthesis genes and actin qRT-PCR used for the experiment were as follows.

```
AsPAL-F:
                                      (SEQ ID NO: 1)
5'-cgatcatggagcacattctg-3'

AsPAL-R:
                                      (SEQ ID NO: 2)
5'-tcgatgacggggttatcatt-3'

AsHHT1-F:
                                      (SEQ ID NO: 3)
5'-ggagaagttccggaagatga-3'
```

```
AsHHT1-R:
                                        (SEQ ID NO: 4)
5'-agaaggggaattttgcagt-3'

AsHHT2-F:
                                        (SEQ ID NO: 5)
5'-ggagaagttccggaagatga-3'

AsHHT2-R:
                                        (SEQ ID NO: 6)
5'-caaagtggcaggaaagaagg-3'

AsHHT3-F:
                                        (SEQ ID NO: 7)
5'-ggagaagttccggaagatga-3'

AsHHT3-R:
                                        (SEQ ID NO: 8)
5'-gaaagaaggggaattttgc-3'

AsHHT4-F:
                                        (SEQ ID NO: 9)
5'-agcccaccaagctgtactgt-3'

AsHHT4-R:
                                        (SEQ ID NO: 10)
5'-ggaccaatgctgacaaatcc-3'

AsActin-F:
                                        (SEQ ID NO: 11)
5'-gctgtgctttccctctatgc-3'

AsActin-R:
                                        (SEQ ID NO: 12)
5'-cgagcttctccttgatgtcc-3'
```

Figure 3:
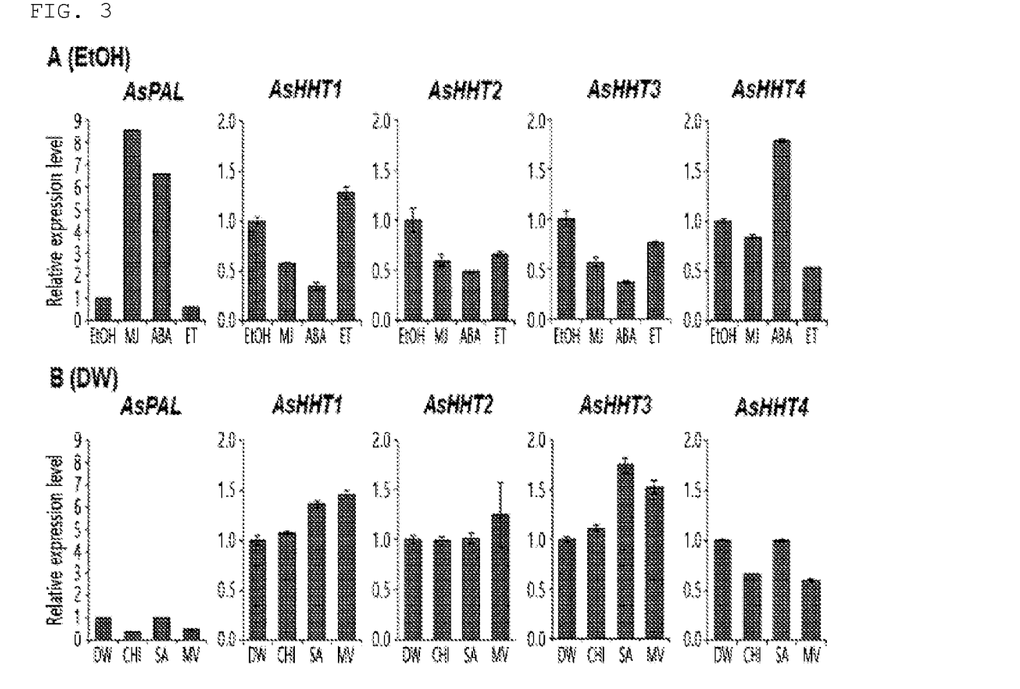
FIG. 3 illustrates a result of analyzing the transcriptional expression of avenanthramide biosynthetic genes PAL and HHT through the treatment with elicitors in oats.

As a result, similarly to Example 3, it was confirmed that the expression of both AsPAL and AsHHT4 genes was increased when MJ and ABA were treated (FIG. 3).

From the results of Examples 3 and 4, it could be seen that MJ and ABA most increased the synthesis amount of avenanthramides in oats compared to other elicitors.

Example 5: Confirmation of Production of Avenanthramides According to Concentration when Treated with Selected Elicitors MJ and ABA An experiment was performed to find an optimal concentration for stably producing avenanthramides by treating the elicitors MJ and ABA selected in Examples 3 and 4 at various concentrations.

Like in Example 3, 10 μM, 20 μM, 25 μM, 50 μM, 75 μM, and 100 μM of MJ and 10 μM, 20 μM, 25 μM, 50 μM, 75 μM, 100 μM, and 300 μM of ABA were treated by concentration on day 2 after germination, recovered on day 5 after germination, then frozen using liquid nitrogen, and stored at −80° C. until extraction and used. As a control, EtOH, a solvent of MJ and ABA, was treated at a concentration of 0.1%. The experimental results were shown in Tables 2 and 3 and FIGS. 4 and 5 below.

TABLE 2

|  | mg/kg, FW | | | | Compared |
| --- | --- | --- | --- | --- | --- |
|  | avnA | avnB | avnC | total | to control |
| Control (EtOH 0.1%) | 68.48 | 128.41 | 46.57 | 243.46 |  |
| 10 μM MJ | 93.22 | 163.98 | 77.35 | 334.55 | 37.41% |
| 20 μM MJ | 98.32 | 168.66 | 86.12 | 353.1 | 45.03% |
| 25 μM MJ | 105.54 | 200.86 | 78.2 | 384.6 | 57.97% |
| 50 μM MJ | 147.03 | 222.81 | 116.59 | 486.43 | 99.80% |

TABLE 2-continued

|  | mg/kg, FW | | | | Compared |
| --- | --- | --- | --- | --- | --- |
|  | avnA | avnB | avnC | total | to control |
| 75 μM MJ | 179.81 | 268.73 | 130.08 | 578.62 | 137.67% |
| 100 μM MJ | 138.82 | 218.47 | 100.73 | 458.02 | 88.13% |

TABLE 3

|  | mg/kg, FW | | | | Compared |
| --- | --- | --- | --- | --- | --- |
|  | avnA | avnB | avnC | total | to control |
| Control (EtOH 0.1%) | 68.48 | 128.41 | 46.57 | 243.46 |  |
| 10 μM ABA | 177.8 | 299.1 | 197.11 | 674.01 | 176.85% |
| 20 μM ABA | 185.34 | 319.67 | 189.65 | 694.66 | 185.33% |
| 25 μM ABA | 202.56 | 363.51 | 226.14 | 792.21 | 225.40% |
| 50 μM ABA | 206.95 | 385.73 | 236.19 | 828.87 | 240.45% |
| 75 μM ABA | 211.62 | 328.63 | 232.94 | 773.19 | 217.58% |
| 100 μM ABA | 186.05 | 309.78 | 197.55 | 693.38 | 184.80% |
| 300 μM ABA | 193.65 | 328.02 | 184.32 | 705.99 | 189.98% |

Figure 4:
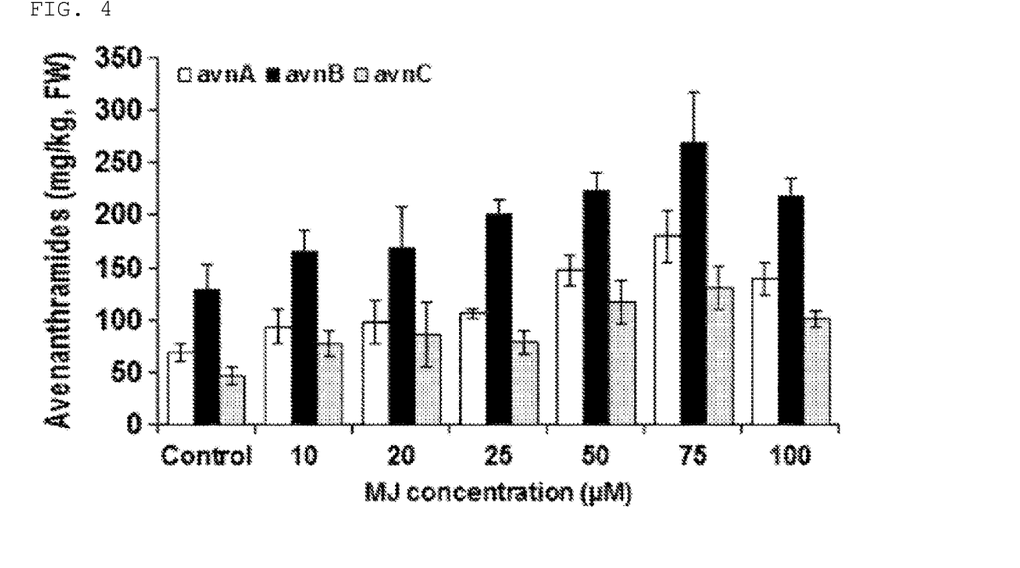
FIG. 4 illustrates a result of comparing material production efficiencies of avenanthramides according to a concentration by treating oats with MJ.

As a result, it was confirmed that the production of avenanthramides was increased at all concentrations treated with MJ, particularly, the production of avenanthramides was increased as the concentration was increased, and that the largest amount of avenanthramides of up to 578.6 mg/kg was produced at a concentration of 75 μM (FIG. 4).

Figure 5:
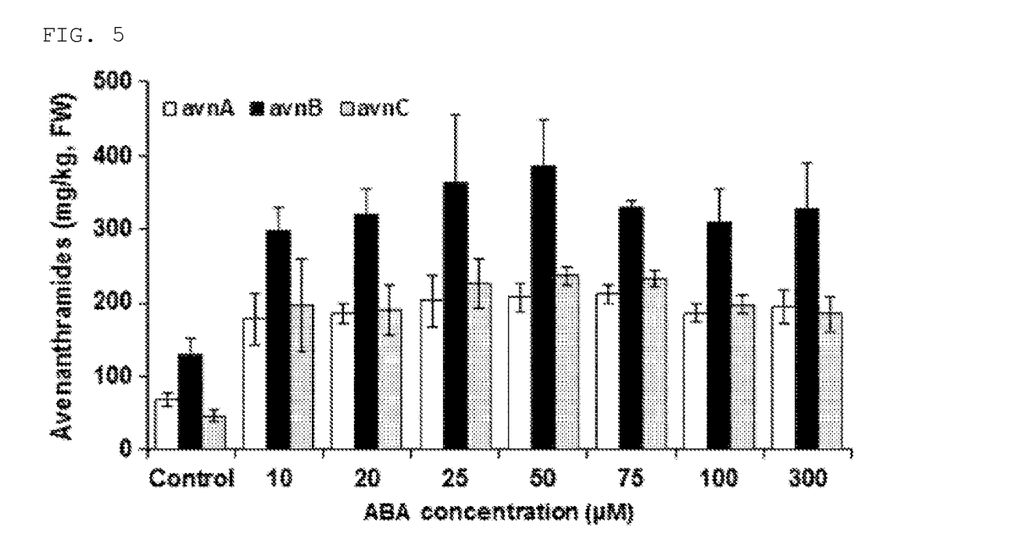
FIG. 5 illustrates a result of comparing material production efficiencies of avenanthramides according to a concentration by treating oats with ABA.

In addition, it was confirmed that the production of avenanthramides also increased at all concentrations during ABA treatment, and it was confirmed that the largest amount of avenanthramides of up to 828.8 mg/kg were produced at a 50 μM concentration (FIG. 5).

Through this, it was confirmed that MJ or ABA may significantly increase the production of avenanthramides in oats, respectively. In addition, it was confirmed that the production of avenanthramides in oats was significantly increased in MJ at concentrations of 10 μM to 100 μM and in ABA at concentrations of 20 to 300 μM.

Example 6: Confirmation of Production Amount of Avenanthramides when Co-Treated with Selected Elicitors MJ and ABA The following experiments were performed to establish optimal conditions for enhancing the production of avenanthramides by simultaneously treating the elicitors MJ and ABA selected in Examples 3 and 4 above.

Specifically, based on the optimal concentrations of 75 μM MJ and 50 μM ABA confirmed in Example 5, oats on day 2 after germination were treated with the elicitors for 3 days while varying concentrations. At day 5 after germination, the oats were recovered, and the contents of avenanthramides were measured and shown in Table 4 and FIG. 6 below. As a control, EtOH, a solvent of MJ and ABA, was treated at a concentration of 0.1%.

TABLE 4

|  | mg/kg, FW | | | | Compared |
| --- | --- | --- | --- | --- | --- |
|  | avnA | avnB | avnC | total | to control |
| Control (EtOH 0.1%) | 70.6 | 132.65 | 43.06 | 246.31 |  |
| 75 μM MJ + 10 μM ABA | 348.55 | 359.44 | 326.23 | 1034.22 | 319.89% |

TABLE 4-continued

| | mg/kg, FW | | | | Compared to control |
|---|---|---|---|---|---|
| | avnA | avnB | avnC | total | |
| 75 μM MJ + 25 μM ABA | 515.59 | 549.95 | 439.82 | 1505.36 | 511.16% |
| 75 μM MJ + 50 μM ABA | 452.63 | 486.1 | 324.94 | 1263.67 | 413.04% |
| 75 μM MJ + 75 μM ABA | 486.91 | 598.19 | 393.38 | 1478.48 | 500.25% |
| 10 μM MJ + 50 μM ABA | 412.84 | 551.15 | 382.51 | 1346.5 | 446.67% |
| 25 μM MJ + 50 μM ABA | 384.06 | 519.82 | 323.71 | 1227.59 | 398.39% |
| 50 μM MJ + 50 μM ABA | 391 | 425.87 | 359.49 | 1176.36 | 377.59% |

As a result, it was confirmed that the production of avenanthramides was increased compared to an untreated group or a single treated group in all the co-treated conditions. In addition, it was confirmed that the largest amount of avenanthramides of up to 1505.3 mg/kg was produced when 75 μM MJ and 25 μM ABA were co-treated among various concentrations (FIG. 6). Through this, it was confirmed that co-treating MJ and ABA very effectively increases the production of avenanthramides.

Example 7: Analysis of Expression of Avenanthramide Biosynthetic Genes when Co-Treated with Selected Elicitors MJ and ABA Based on the results performed in Example 6, transcriptional expression analysis was performed.

qRT-PCR was performed using the same primers as in Example 4, and as a result, it was confirmed that the expression of AsPAL and AsHHT4 increased the most when MJ and ABA were co-treated.

Through this, it was found that the expression of avenanthramide biosynthesis genes increased by co-treatment with MJ and ABA, and the biosynthesis amount of avenanthramides was significantly increased. In addition, it was confirmed that HHT4 was a gene that specifically responded to MJ and ABA among genes encoding HHT.

It will be appreciated by those skilled in the art that the present invention as described above may be implemented into other specific forms without departing from the technical spirit or essential characteristics thereof. Thus, it is to be appreciated that embodiments described above are intended to be illustrative in every sense and not restrictive. The scope of the present invention is represented by claims to be described below rather than the detailed description, and it is to be interpreted that the meaning and scope of the claims and all changes or modified forms derived from the equivalents thereof come within the scope of the present invention.

The invention claimed is:

1. A method for producing oats having high-content of avenanthramides, the method comprising incubating oat seeds for 2 days to induce germination of the oat seeds, and treating germinated oats with 10 μM to 75 μM of methyl jasmonate and 10 μM to 75 μM of abscisic acid after incubating the oat seeds for 2 days,
wherein the oats have high-content avenanthramides compared to oats untreated with methyl jasmonate and abscisic acid, and
wherein the avenanthramides are selected from the group consisting of avenanthramides A, B and C.

2. The method of claim 1, wherein the germinated oats are treated with methyl jasmonate and abscisic acid for 12 to 144 hours.

3. The method of claim 1, wherein the germinated oats are treated with methyl jasmonate and abscisic acid at a concentration ratio of 4:1 to 1:1.

4. A method for producing avenanthramides, the method comprising:
incubating oat seeds for 2 days to induce germination of the oat seeds, and treating germinated oats with 10 μM to 75 μM of methyl jasmonate and 10 μM to 75 μM of abscisic acid after incubating the oat seeds for 2 days;
obtaining an extract or fraction of the oats; and
obtaining avenanthramides from the extract or fraction,
wherein the avenanthramides are selected from the group consisting of avenanthramides A, B and C.

5. A method for increasing the expression of avenanthramide biosynthetic genes in oats, the method comprising incubating oat seeds for 2 days to induce germination of the oat seeds, and treating germinated oats with 10 μM to 75 μM of methyl jasmonate and 10 μM to 75 μM of abscisic acid after incubating the oat seeds for 2 days,
wherein the avenanthramide biosynthetic genes are AsPAL or AsHHT4.

6. The method of claim 1, wherein the oat seeds are incubated at 4° C. for 2 days to induce germination of the oat seeds.

7. The method of claim 1, wherein the germinated oats are treated with methyl jasmonate and abscisic acid for 3 days.

8. The method of claim 4, wherein the oat seeds are incubated at 4° C. for 2 days to induce germination of the oat seeds.

9. The method of claim 4, wherein the germinated oats are treated with methyl jasmonate and abscisic acid for 3 days.

10. The method of claim 5, wherein the oat seeds are incubated at 4° C. for 2 days to induce germination of the oat seeds.

11. The method of claim 5, wherein the germinated oats are treated with methyl jasmonate and abscisic acid for 3 days.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: AsPAL-F

<400> SEQUENCE: 1
cgatcatgga gcacattctg                                          20

<210> SEQ ID NO 2
<211> LENGTH: 20
<212> TYPE: DNA
<213> ORGANISM: Artificial Sequence
<220> FEATURE:
<223> OTHER INFORMATION: AsPAL-R

<400> SEQUENCE: 2
tcgatgacgg ggttatcatt                                          20

<210> SEQ ID NO 3
<211> LENGTH: 20
<212> TYPE: DNA
<213> ORGANISM: Artificial Sequence
<220> FEATURE:
<223> OTHER INFORMATION: AsHHT1-F

<400> SEQUENCE: 3
ggagaagttc cggaagatga                                          20

<210> SEQ ID NO 4
<211> LENGTH: 20
<212> TYPE: DNA
<213> ORGANISM: Artificial Sequence
<220> FEATURE:
```

```
<223> OTHER INFORMATION: AsHHT1-F

<400> SEQUENCE: 4 agaagggga attttgcagt                                                    20

<210> SEQ ID NO 5
<211> LENGTH: 20
<212> TYPE: DNA
<213> ORGANISM: Artificial Sequence
<220> FEATURE:
<223> OTHER INFORMATION: AsHHT2-F

<400> SEQUENCE: 5
ggagaagttc cggaagatga                                                   20

<210> SEQ ID NO 6
<211> LENGTH: 20
<212> TYPE: DNA
<213> ORGANISM: Artificial Sequence
<220> FEATURE:
<223> OTHER INFORMATION: AsHHT2-R

<400> SEQUENCE: 6
caaagtggca ggaaagaagg                                                   20

<210> SEQ ID NO 7
<211> LENGTH: 20
<212> TYPE: DNA
<213> ORGANISM: Artificial Sequence
<220> FEATURE:
<223> OTHER INFORMATION: AsHHT3-F

<400> SEQUENCE: 7
ggagaagttc cggaagatga                                                   20

<210> SEQ ID NO 8
<211> LENGTH: 20
<212> TYPE: DNA
<213> ORGANISM: Artificial Sequence
<220> FEATURE:
<223> OTHER INFORMATION: AsHHT3-R

<400> SEQUENCE: 8
gaaagaaggg ggaattttgc                                                   20

<210> SEQ ID NO 9
<211> LENGTH: 20
<212> TYPE: DNA
<213> ORGANISM: Artificial Sequence
<220> FEATURE:
<223> OTHER INFORMATION: AsHHT4-F

<400> SEQUENCE: 9
agcccaccaa gctgtactgt                                                   20

<210> SEQ ID NO 10
<211> LENGTH: 20
<212> TYPE: DNA
<213> ORGANISM: Artificial Sequence
<220> FEATURE:
<223> OTHER INFORMATION: AsHHT4-R

<400> SEQUENCE: 10
ggaccaatgc tgacaaatcc                                                   20
```

```
<210> SEQ ID NO 11
<211> LENGTH: 20
<212> TYPE: DNA
<213> ORGANISM: Artificial Sequence
<220> FEATURE:
<223> OTHER INFORMATION: AsActin-F

<400> SEQUENCE: 11
gctgtgcttt ccctctatgc                                               20

<210> SEQ ID NO 12
<211> LENGTH: 20
<212> TYPE: DNA
<213> ORGANISM: Artificial Sequence
<220> FEATURE:
<223> OTHER INFORMATION: AsActin-R

<400> SEQUENCE: 12
cgagcttctc cttgatgtcc                                               20
```